United States Patent [19]

Vaahs et al.

[11] Patent Number: 5,219,972
[45] Date of Patent: Jun. 15, 1993

[54] PROCESS FOR THE PREPARATION OF POLYMERIC CHLOROSILAZANES

[75] Inventors: Thilo Vaahs, Kelkheim; Hans-Jerg Kleiner, Kronberg/Taunus, both of Fed. Rep. of Germany

[73] Assignee: Hoechst Aktiengesellschaft, Frankfurt am Main, Fed. Rep. of Germany

[21] Appl. No.: 771,323

[22] Filed: Oct. 2, 1991

[30] Foreign Application Priority Data

Oct. 4, 1990 [DE] Fed. Rep. of Germany ....... 4031315

[51] Int. Cl.$^5$ .............................................. C08G 77/12
[52] U.S. Cl. ........................................ 528/31; 528/33; 528/34; 525/477; 525/478
[58] Field of Search ............................ 528/31, 33, 34; 525/477, 478

[56] References Cited

U.S. PATENT DOCUMENTS

| 5,008,423 | 4/1991 | Gerdau et al. | 528/31 |
| 5,011,801 | 4/1991 | Vaahs et al. | 501/97 |
| 5,032,663 | 7/1991 | Vaahs et al. | 528/31 |
| 5,100,975 | 3/1992 | Vaahs et al. | 528/34 |

FOREIGN PATENT DOCUMENTS 2004401 6/1990 Canada .

Primary Examiner—Melvyn I. Marquis

[57] ABSTRACT

The invention relates to a process for the preparation of polymeric chlorosilazanes by reaction of oligomeric silazanes with chlorosilanes under at least 30 bar at 250° to 400° C.

8 Claims, No Drawings

PROCESS FOR THE PREPARATION OF POLYMERIC CHLOROSILAZANES

The invention relates to a process for the preparation of polymeric chlorosilazanes by reaction of oligomeric silazanes with at least one chlorosilane. This reaction is already known under atmospheric pressure from DE-OS 38 40 779. However, a certain amount of insoluble ammonium chloride is always formed under these conditions. This must be filtered off, or it sublimes on colder parts of the apparatus, the lines leading away easily becoming obstructed In addition, a high reflux is necessary with this type of preparation.

It is furthermore mentioned that the reaction can also be carried out under pressures of up to 10 bar, although this does not prevent the occurrence of insoluble residues.

All these disadvantages are surprisingly avoided by carrying out the reaction under a pressure of at least 30 bar.

The present invention thus relates to a process for the preparation of polymeric chlorosilazanes by reaction of oligomeric silazanes of the formula (I)

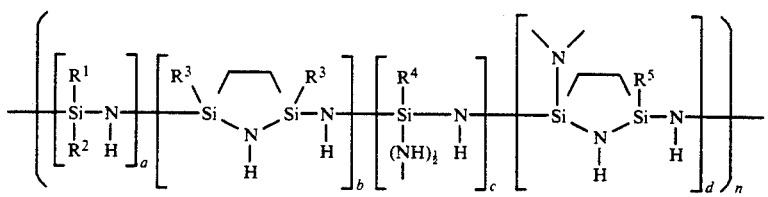

in which at least one of the indices a and b is not 0 and n is about 2 to 12, with at least one of the chlorosilanes $Cl_2R^6Si-CH_2CH_2-SiR^6Cl_2$, $Cl_3Si-CH_2CH_2-SiR^7Cl_2$, $R^8SiCl_3$ or $R^9SiHCl_2$, in which, independently of one another, $R^1$, $R^2$, $R^4$, $R^8$ and $R^9 = H$, $C_1-C_6$-alkyl or $C_2-C_6$-alkenyl and $R^3$, $R^5$, $R^6$ and $R^7 = C_1-C_6$-alkyl or $C_2-C_6$-alkenyl, which comprises carrying out the reaction under at least 30 bar at 250° to 400° C. The reaction is preferably carried out under at least 50 bar at 280° to 320° C.

At least some of the pressure is generated by the vapor pressure of the substances in the reaction vessel at the reaction temperature chosen, that is to say by their "autogenous pressure". If the autogenous pressure at the reaction temperature is already at least 30 bar, it is not necessary to generate a pressure higher than the autogenous pressure by addition of $N_2$ or a noble gas, in particular argon; however, this may sometimes be advantageous. If, however, the autogenous pressure at the reaction temperature chosen is less than 30 bar, an overall pressure of at least 30 bar is generated in the reaction vessel by the addition of inert gas mentioned. In general, the overall pressure will not exceed 150 bar.

The maximum possible value of the autogenous pressure depends on the substances used (oligomeric silazane, chlorosilane and preferably also the solvent used), and would in each case be achieved by using a temperature of 400° C. if such a temperature were to be used, although this is not preferred.

For the radicals $R^1$ to $R^9$ in the compounds reacted with one another, preferably: $R^1$, $R^2$, $R^4$, $R$ and $R^9 = H$, $C_1-C_3$-alkyl or $C_2-C_3$-alkenyl and $R^3$, $R^5$, $R^6$ and $R^7 = C_1-C_3$-alkyl or $C_2-C_3$-alkenyl.

a, b, c and d are the molar fractions of the particular structural units, wherein $a+b+c+d=1$.

The oligomeric silazanes of the formula (I) used as starting substances can be obtained by reacting excess ammonia with a starting material which contains at least one of the two components (II) $R^1R^2SiCl_2$ and (III) $Cl_2R^3Si-CH_2CH_2-SiR^3Cl_2$ and furthermore can contain (IV) $R^4SiCl_3$ and (V) $Cl_3Si-CH_2CH_2-SiR^5Cl_2$, at $-70°$ C. to 100° C., it being possible for $R^1$ to $R^5$ to assume the above meanings and for the molar percentage content of (II) or (III) or the mixture thereof to be 30 to 100 mol %. This corresponds to the following values of the molar fractions a, b, c and d in the oligomeric silazane:

$a+b=0.3$ to $1.0$ $c+d=0.0$ to $0.7$ in which a can be 0 or b can be 0, but a and b can never simultaneously assume the value 0. In contrast, c and d can also simultaneously assume the value 0. Precisely when a chlorosilane (IV) is employed, c is $>0$. Analogously, d is $>0$ precisely when a chlorosilane (V) is used.

The compounds (II) and (IV) used as starting materials for the oligomeric silazanes are commercially available, and the ethylene-bridged species (III) and (V) are accessible by hydrosilylation of commercially available $R^3HSiCl_2$ and ethine or by hydrosilylation of vinyltrichlorosilane and $R^5HSiCl_2$.

The molar ratio of the reactants chlorosilane: monomer unit of the oligomeric silazane (n=1) in the reaction to give the polymeric chlorosilazane is preferably about 0.1:1 to about 1.5:1, in particular about 0.1:1 to about 0.7:1.

It is additionally advantageous to carry out the reaction in a solvent which does not react with the reaction components. Suitable solvents are ether or hydrocarbons. The reaction in the solvent has the advantage that the solid polysilazane formed does not have to be dissolved out of the reaction vessel, but is already present in solution and the reaction vessel can thus be charged and emptied in a simple manner.

The chlorosilazanes prepared according to the invention can be converted into material containing $Si_3N_4$ by treatment with $NH_3$ and subsequent pyrolysis, as described in DE-OS 38 40 779.

EXAMPLES

Example 1

Reaction of $-(-CH_3SiH-NH-)-_n$ with $CH_3SiHCl_2$ without a solvent 20 ml (22.3 g; 0.19 mol) of $CH_3SiHCl_2$ were added to 50 g (0.85 mol; based on n=1) of $-(-CH_3SiH-NH-)-_n$, that is to say the compound (I) where $a=1$ and $b=c=d=0$, at $-15°$ C. and the components were mixed completely. After the reaction mixture had thawed, it was introduced into a VA autoclave of 250 ml capacity, this being flushed with dry nitrogen before and during the introduction.

After the autoclave had been closed, it was heated up to an internal temperature of 300° C. in the course of 4 hours. This temperature was maintained for 2 hours and the autoclave was then allowed to cool.

The final pressure at 300° C. in this reaction was 156 bar. After the autoclave had been let down, it was opened and the solid polymeric silazane was dissolved out with tetrahydrofuran under an inert gas and then freed from the solvent.

A vitreous substance remained, which had a defined softening point of 125° C.

| Elemental analysis (% by weight) | Si 42.1% |
|---|---|
| | N 15.3% |
| | Cl 18.9% |
| | C 15.2% |
| | H 7.3% |

The ceramic yield in $N_2$ was 72%, and the black ceramic prepared in this way had carbon contents of 11.4%.

The ceramic yield in $NH_3$ was 56%, the ceramic prepared in this way no longer containing carbon.

Example 2

Reaction of —(—CH₃SiH—NH—)—$_n$ with CH₃SiHCl₂ in diphenylmethane 50 g (0.85 mol; based on n=1) of —(—CH₃SiH—NH—)—$_n$, that is to say the compound (I) where a=1 and b=c=d=0, were dissolved in 50 ml of diphenylmethane and the solution was mixed with 22.3 g (0.19 mol) of CH₂SiHCl₂ at 20° C.

This solution was introduced into a VA autoclave of 250 ml capacity, which was previously flushed with nitrogen. After the autoclave had been closed, it was heated up to 300° C. in the course of 4 hours. This temperature was maintained for 3 hours and the autoclave was then allowed to cool. The final pressure at 300° C. in this reaction was 190 bar. After the autoclave had been opened, the clear solution was freed from the solvent.

67 g of a clear substance which had solidified in vitreous form and had a softening point of 150° C. remained.

| Elemental analysis (% by weight) | Si 41.7% |
|---|---|
| | N 15.1% |
| | Cl 20.9% |
| | C 14.8% |
| | H 7.1% |

Example 3

The procedure was as in Example 2 with 50 ml of diphenylmethane as the solvent, but with the following reactants:

50 g (0.35 mol) of

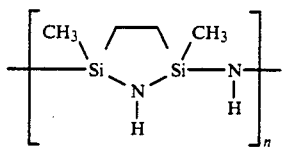

(compound (I) where a=c=d=0 and b=1)
10.2 g (0.07 mol) of CH₃SiCl₃
Final pressure: 45 bar (established with the aid of added $N_2$).
Yield: 45 g of polymeric chlorosilazane with a softening point of about 115° C.

| Elemental analysis (% by weight) | Si 38.4% |
|---|---|
| | C 26.8% |
| | N 13.2% |
| | Cl 10.4% |
| | O 0.7% |

Example 4

The procedure was as in Example 2 with 50 ml of diphenylmethane as the solvent, but with the following reactants:

50 g (0.35 mol) of

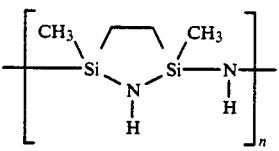

(compound (I) where a=c=d=0 and b=1)
17.7 g (0.07 mol) of Cl₂(CH₃)Si—CH₂CH₂—Si(CH₃)Cl₂
Final pressure: 100 bar (established with the aid of added $N_2$).
Yield: 51.4 g of polymeric chlorosilazane with a softening point of about 130° C.

| Elemental analysis (% by weight) | Si 37.1% |
|---|---|
| | C 28.2% |
| | N 12.2% |
| | Cl 9.9% |

Example 5

The procedure was as in Example 2 with 50 ml of diphenylmethane as the solvent, but with the following reactants:

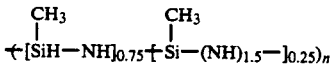

(compound (I) where a=0.75, c=0.25 and b=d=0)
38.1 g (0.23 mol) of vinyltrichlorosilane
Final pressure: 104 bar (without addition of inert gas, that is to say only the autogenous pressure).
Yield: 56.4 g of polymeric chlorosilazane with a softening point of about 125° C.

| Elemental analysis (% by weight) | Si | 39.4% |
|---|---|---|
| | C | 16.8% |
| | N | 15.4% |
| | Cl | 14.3% |

Example 6

The procedure was as in Example 2 with 50 ml of diphenylmethane as the solvent, but with the following reactants:

50 g of

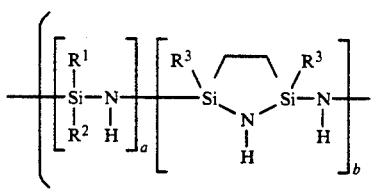

(compound (I) where $a=0.6$, $b=0.1$, $c=0.2$ and $d=0.1$)

40.3 g (0.25 mol) of vinyltrichlorosilane

Final pressure: 95 bar (without addition of inert gas, that is to say only the autogenous pressure).

Yield: 61.4 g of polymeric chlorosilane with a softening point of about 165° C.

| Elemental analysis (% by weight) | Si | 38.5% |
|---|---|---|
| | C | 18.3% |
| | N | 16.1% |
| | Cl | 12.9% |

We claim:

1. A process for the preparation of a polymeric chlorosilazane by reaction of an oligomeric silazane of the formula (I)

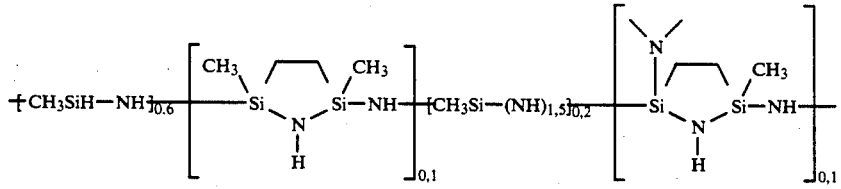

in which the index a plus the index b is a number from 0.3 to 1.0, the index c plus the index d is a number from 0.0 to 0.7, at least one of the indices a and b is not 0 and n is about 2 to 12, with at least one of the chlorosilanes $Cl_2R^6Si-CH_2CH_2-SiR^6Cl_2$, $Cl_3Si-CH_2CH_2-SiR^7Cl_2$, $R^8SiCl_3$ or $R^9SiHCl_2$, in which, independently of one another $R^1$, $R^2$, $R^4$, $R^8$ and $R^9=H$, $C_1-C_6$-alkyl or $C_2-C_6$-alkenyl and $R^3$, $R^5$, $R^6$ and $R^7=C_1-C_6$-alkyl or $C_2-C_6$-alkenyl, which comprises carrying out the reaction under at least 30 bar at 250° to 400° C.

2. The process as claimed in claim 1, wherein the reaction is carried out under at least about 50 bar at about 280° to 320° C.

3. The process as claimed in claim 1, wherein the reaction is carried out in an ether solvent or hydrocarbon solvent.

4. The process as claimed in claim 2, wherein the reaction is carried out in an ether solvent or hydrocarbon solvent.

5. The process as claimed in claim 1, wherein the reaction is carried out under a pressure not exceeding about 150 bar.

6. The process as claimed in claim 5, wherein the reaction is carried out under at least 50 bar.

7. The process as claimed in claim 6, wherein the process is carried out at a temperature in the range of about 250° to about 320° C.

8. The process as claimed in claim 1, wherein the total of the indices $a+b+c+d$ is 1.

* * * * *